United States Patent [19]

Tieman

[11] Patent Number: 4,866,045
[45] Date of Patent: Sep. 12, 1989

[54] TETRACHLOROETHYL PHOSPHOROTHIOATE SOIL INSECTICIDE

[75] Inventor: Charles H. Tieman, Modesto, Calif.

[73] Assignee: E. I. Du Pont Nemours and Company, Wilmington, Del.

[21] Appl. No.: 275,958

[22] Filed: Nov. 25, 1988

Related U.S. Application Data

[63] Continuation of Ser. No. 82,996, Aug. 7, 1987, abandoned, which is a continuation of Ser. No. 605,093, Apr. 30, 1984, abandoned.

[51] Int. Cl.$^4$ ............................................. A01N 57/10
[52] U.S. Cl. ................................................... 514/144
[58] Field of Search ........................................... 514/144

[56] References Cited

U.S. PATENT DOCUMENTS

| | | | |
|---|---|---|---|
| 3,027,296 | 3/1962 | Whetstone | 167/22 |
| 3,080,274 | 3/1963 | Ugator et al. | 424/225 |
| 3,184,377 | 5/1965 | Hensel et al. | 167/22 |
| 3,258,507 | 6/1966 | Hensel et al. | 260/963 |
| 3,705,941 | 12/1972 | Hennart et al. | 424/219 |
| 3,732,341 | 5/1973 | Sirrenberg et al. | 260/950 |
| 3,781,428 | 12/1973 | Hennart et al. | 424/219 |
| 3,845,174 | 10/1974 | Sirrenberg et al. | 260/963 |
| 4,235,891 | 11/1980 | Saito et al. | 424/224 |
| 4,457,923 | 7/1984 | Fahmy | 424/224 |

FOREIGN PATENT DOCUMENTS

| | | | |
|---|---|---|---|
| 0745483 | 8/1970 | Belgium | 424/225 |
| 107581 | 8/1974 | Fed. Rep. of Germany. | |
| 123096 | 11/1976 | Fed. Rep. of Germany. | |
| 2038467 | 1/1971 | France. | |
| 2040953 | 1/1971 | France. | |
| 1330788 | 9/1973 | United Kingdom. | |

*Primary Examiner*—Allen J. Robinson

[57] ABSTRACT

A method for controlling insect larvae which inhabit the soil and feed on growing plants selected from rootworms, cutworms and wireworms which comprises applying to the soil habitat of the larvae an insecticidally-effective amount of 0,0-diethyl 0-(1,2,2,2-tetrachloroethyl)phosphorothioate.

23 Claims, No Drawings

TETRACHLOROETHYL PHOSPHOROTHIOATE SOIL INSECTICIDE

This application is a continuation of application Ser. No. 082,996 filed Aug. 7, 1987, now abandoned, which is a continuation of Ser. No. 605,093, filed Apr. 30, 1984, now abandoned.

BACKGROUND OF THE INVENTION

1. Field of the Invention

The present invention relates to a method of controlling certain soil inhibiting larvae with O,O-diethyhl O-(1,2,2,2-tetrachloroethyl)phosphorothioate.

2. Description of the Prior Art

U.S. Pat. No. 3,027,296 describes a number of halogenated phosphorus esters, including O,O-diethyl O-(1,2,2,2-tetrachloroethyl)phosphorothioate at columns 7 and 8, as insecticides. This patent shows testing of certain of the halogenated phosphorus esters for insecticidal activity on houseflies, two-spotted mites and pea aphids. None of these tests involved application and use of these halogenated phosphorus compounds as soil insecticides in the soil habitat of insects or their larvae. The patent suggests that the compounds have systemic insecticidal activity when applied to the soil in the vicinity of growing plants or directly to the plants.

East German Pat. No. 123,096 also discloses various polyhaloalkyl phosphate esters, including O,O-dimethyl and O,O-diethyl O-(1,2,2,2-tetrachloroethyl)-phosphorothioate as compounds 41 and 42, and broadly their use as insecticides.

Several commercial materials are used for control of soil insects or their larvae, which feed on growing plants, including Diazinon insecticide:
O,O—diethyl O—(2-isopropyl-4-methyl-6-pyrimidinyl)phosphorothioate

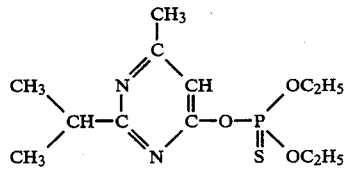

Furadan insecticide:
2,3-dihydro-2,2-dimethyl-7-benzofuranyl methylcarbamate

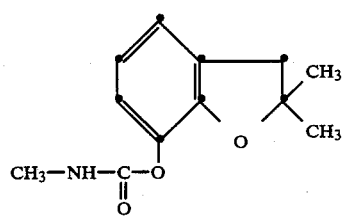

Lorsban insecticide:
O,O—diethyl O—(3,5,6-trichloro-2-pyridinyl) phosphorothioate

-continued

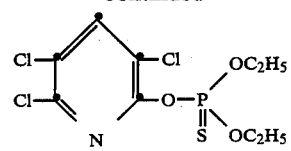

Counter insecticide:
S—(((1,1-dimethylethyl)thio)methyl) O,O—diethyl phosphorodithioate

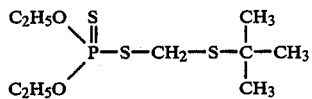

None of these commercial materials provides the high degree of control of insect larvae which inhabit the soil and feed on growing plants that is afforded by the tetrachloroethyl phosphorothioate of the present invention.

SUMMARY OF THE INVENTION

The present invention is directed to a method of controlling insect larvae which inhabit the soil and feed on growing plants selected from rootworms, cutworms and wireworms, which comprises applying to the soil habitat of the larvae an insecticidally effective amount of O,O-diethyl O-(1,2,2,2-tetrachloroethyl)phosphorothioate.

O,O-Diethyl O-(1,2,2,2-tetrachloroethyl)phosphorothioate has unexpectedly high activity against certain insect larvae which inhabit the soil and feed on growing plants by virtue of its application to the soil habitat and its persistent effectiveness over an extended period of time. Since the various kinds of soil-inhabiting larvae to be controlled do not manifest a problem at the same period of time, it is especially difficult to effectively control these larvae by one application of a larvicide before the plants, which might be damaged by the larvae, have even emerged. For example, the black cutworm is often a seve pest in seedling corn where usually two to three weeks following corn planting they infest the ground, near, yet beneath its surface, and cut the seedling off at ground level. By contrast, the corn rootworm infestation is a severe problem usually five to seven weeks after corn planting, and these worms infest the ground, up to six inches below the surface, chewing on the roots of the corn. In the case of wireworms, the infestation can occur throughout the growing season in which the wireworms infest the ground and attack the seed, the underground stem or the roots.

To control the larvae by application before the plant has emerged requires a material that is effective for an extended period of time and has a mode of action which is other than systemic. Thus, the material to control larvae, which inhabit the soil and feed upon plants, should have persistence as well as larvicidal activity other than systemic insecticidal activity.

The material of the invention is useful for controlling a variety of insect larvae in the soil that are damaging to growing plants, including viable seeds thereof. The effectiveness of this material as a soil insecticide for protecting growing plants is surprising in view of the generally low foliar activity of the material. The material of the invention is well suited for the control of Diabrotica species, for example, *Diabrotica virgifera* LeConte, *Diabrotica longicornis* (Say), and *Dabrotica*

*undecimpunctata howardi* Barber, the western, northern and southern corn rootworm, respectively, and *Diabrotica undecimpunctata undecimpunctata* Mannerheim, particularly in their larval stages. Because the material of the invention have unusually good larvicidal activity, they may be advantageously used against rootworms, cutworms and wireworms, for example, larvae of Diabrotica (rootworms), Agrotis, Crymodes, Amathes, Euxoa, Peridroma, Lacinipolia, NephelodesActebia, Feltia, Loxagrotis (cutworms), Agriotes, Limonius, Horistonotus, Ctenicera, Conoderus (wireworms) and the like. Some of the better known larval species of the above are: *Agrotis ipsilon* (Hufnagel) (black cutworm), *Agriotes mancus* (Say) (wheat wireworm) and particularly the three Diabrotica species mentioned above.

The material of the invention can be conveniently formulated for use as granules or powders containing a solid diluent, impregnated with the material of the invention. Such formulations usually contain from about 1 to 50% by weight of the material of the invention. More effective control will result when the formulation is physically lightly mixed with the topsoil. The mixing isconcurrent with, preceded or followed by planting seed which germinate into plants.

The material of the invention can be applied as a drench, that is as a solution or dispersion of the material of the invention in a non-phytotoxic solvent or liquid diluent, suitably water. Such drenches can be prepared by diluting with water a concentrate containing the materials of the invention, an emulsifying agent, and preferably an organic solvent such as toluene. The material of the invention can be applied as a band, furrow or side dress, either incorporated or not.

The material of the invention is suitably applied to the soil at a rate of from about 0.01 to about 11 kg/ha. Good control of soil inhabiting insects is obtained at rates of from about 0.1 to about 5 kg/ha, and especially from about 0.5 to about 4 kg/ha.

The O,O-diethyl O-(1,2,2,2-tetrachloroethyl)phosphorothioate used in the present invention can be prepared by various conventional methods of preparing phosphorus thioesters. In one such method chloral is treated with phosphorus pentachloride to give $CCl_3CHClOPCl_4$, which is treated with hydrogen sulfide to give the intermediate $CCl_3CHClOP(S)Cl_2$. This dichloridate is treated with ethanol to give the desired ester of the present invention. For this reaction with ethanol, an inert solvent can be present, but the reaction proceeds satisfactorily in the absence of a solvent. This reaction is preferably conducted at less than ambient temperatures by use of a cooling system, such as an ice bath. The addition of a conventional buffering agent, such as an alkali metal bicarbonate, is desirable. The reaction proceeds to completion after several hours or days. The resulting product mixture is diluted with an inert solvent, such as methylene chloride, washed, filtered and stripped of solvent. The crude product can be purified by one or more of the conventional methods of distillation, chromatography and extraction using inert solvents.

ILLUSTRATIVE EMBODIMENTS

The invention is illustrated by the following embodiments which describe the preparation of the compound of the invention and its use to control soil larvae (worms).

Embodiment 1—O,O-Diethyl O-(1,2,2,2-tetrachloroethyl)phosphorothioate

To 31.6 g of phosphorus pentachloride in 100 ml of carbon tetrachloride at 35° C. was added dropwise over ½ hour a mixture of 0.1 ml of acetonitrile and 9.8 ml of chloral. The reaction mixture was maintained at 34°–35° C. overnight, filtered, and the filtrate was cooled with ice. Hydrogen sulfide was bubbled through the cooled filtrate in an amount of 13.7 g over 3 hours. The reaction mixture was allowed to warm for a short time and the solvent was evaporated to leave 31.4 g of a yellow liquid, which was distilled in a kugelrohr at 60°–70° C. (0.1 mm) to give 10.3 g of yellow liquid mixed with some black solid. This material was vacuum chromatographed using hexane to give 9.1 g of O-(1,2,2,2-tetrachloroethyl)phosphorothiodichloridate.

To 3.2 g of O-(1,2,2,2-tetrachloroethyl)phosphorothiodichloridate was added 25 ml of ethanol. The reaction mixture was cooled for 45 minutes with ice and then an excess of sodium bicarbonate was added. After 3 days, the mixture was diluted with methylene chloride and washed with water. The separated organic phase was dried, evaporated and kugelrohr distilled at 75°–85° C. (0.05 mm) to give 2.0 g of liquid, which was vacuum chromatographed using hexane to yield 1.4 g of the desired product as a colorless liquid.

Embodiment 2—Corn Rootworm Test

The phosphorothioate of the invention is dissolved in acetone solvent and thoroughly incorporated into dry soil. After venting traces of solvent, the soil moisture level is brought to 9% by adding water and thoroughly mixing.

60 g of moist soil is added to a 4 oz wide-mouthed jar to ½ full. Two sweet corn seeds, which have been surface sterilized in 0.2% sodium hypochlorite solution for 15 minutes and rinsed with water, are pressed into the soil near the perimeter of the jar. A small cavity of about 2.5 cc is opened in the surface of the soil and 20 *Diabrotica undecimpunctata undecimpunctata* Mannerheim (western spotted cucumber beetle) eggs are placed in the well. They are immediately covered over with fine-seived Zololite or Vermiculite and the covering material is wet with about 1.5 cc of water. The jar is then capped with a lid into which two 2 mm holes have been drilled for ventilation. The jars are placed under lamps at 27° C. for holding. The eggs are generaly two to four days old.

After one week, the jar contents are examined for the presence of live larvae and the number is recorded and the corn roots are examined for feeding damage. Compounds showing control at 3 ppm or lower rate in the first week are evaluated at subsequent weeks. Activity at 3 ppm indicates viable soil insecticidal activity.

Results of tests with the phosphorothioate of the invention are shown in in the Table I below and are expressed by the following ratings.

| Rating | Control Potential | Larval Count |
|---|---|---|
| 0 | Complete control | 0 |
| 1 | Excellent | >0 to <3 |
| 2 | Good | >3 to <6 |
| 3 | Fair | >6 to <10 |
| 4 | Poor | >10 |

Results of corn rootworm tests with commercial materials Counter insecticide, Furadan insecticide, and Lorsban insecticide are also set forth in Table I.

TABLE I

RESULTS OF CORN ROOTWORM TEST

| Compound | PPM | Rating at Weeks after Application | | | |
|---|---|---|---|---|---|
| | | 0 | 2 | 4 | 8 |
| Embodiment 1 | 1.0 | 0 | 0 | 0 | 0 |
| | 0.3 | 0 | 0 | 0 | 0 |
| | 0.1 | 0 | 0 | 0 | 0 |
| | 0.05 | 0 | 1 | 1 | 1 |
| | 0.025 | 0 | 1 | 2 | 2 |
| | 0.01 | 1 | 3 | 3 | 4 |
| Counter | 1.0 | 0 | 0 | 0 | 0 |
| | 0.3 | 0 | 1 | 0 | 0 |
| | 0.1 | 4 | 4 | 4 | 3 |
| Furadan | 1.0 | 0 | 0 | 0 | 0 |
| | 0.3 | 0 | 1 | 1 | 1 |
| | 0.1 | 2 | 4 | — | — |
| Lorsban | 1.0 | 0 | 0 | 0 | 0 |
| | 0.3 | 0 | 0 | 0 | 0 |
| | 0.1 | 1 | 1 | 1 | — |
| | 0.05 | 3 | 4 | 3 | — |

— "means" no test.

Embodiment 3—Black Cutworm Test

Air-dried field soil, screened to remove debris and clods, is used for this test. The soil contains approximately 1% residual moisture. Two hundred grams of soil is weighed and placed in a 500 ml nalgene bottle. Screening rates for the test compounds are 2 ppm and 20 ppm, made up in 18 ml of Atlox 1045A (0.05%) water. This 18 ml solution is poured into the 200 grams of soil, resulting in a 10% soil moisture content. The bottles containing the treated soil are then capped and the samples of soil allowed to sit for approximately 30 minutes. The soil is then vigorously shaken to thoroughly mix the compound and soil. Two 60 g sub-samples are weighed from the original 200 g sample and placed in a 4 oz wide-mouth jars. A small cavity is made in the surface of the soil and a 10 mm square plug of artificial diet is placed in the well. Five holes are then pressed into the soil surrounding the diet, approximately 15 mm deep and 6 mm in diameter. A single third instar Black Cutworm larvae [agrotis ipsilon (Hufnagel)] is placed into each hole and then covered with soil. The jars are fitted with plastic screw cap lids, which have two 2 mm holes drilled in the top. Jars are held for 48 hours, at which time results are observed and recorded. Lorsban, which is the principal material registered for cutworm control at planting time, is the standard used in this test and provides 90–100% mortality at 2 ppm. Results are set forth in Table II.

TABLE II

RESULTS OF BLACK CUTWORM TEST

| Compound | PPM | % Mortality |
|---|---|---|
| Embodiment 1 | 20 | 100 |
| | 2 | 100 |
| | 1 | 100 |
| | 0.5 | 100 |
| | 0.25 | 20 |
| | 0.1 | 0 |
| Lorsban | 20 | 100 |
| | 2 | 100 |
| | 1 | 40 |
| | 0.5 | 0 |

What is claimed is:

1. A method for controlling insect larvae which inhabit the soil and feed on growing plants selected from rootworms, cutworms or wireworms which comprises applying to the soil habitat of the larvae an insecticidally effective amount of the soil insecticide, O,O-diethyl O-(1,2,2,2-tetrachloroethyl)phosphorothioate for controlling the insect larvae for at least 28 days.

2. A method according to claim 1 wherein the insect larvae are selected from rootworms or cutworms.

3. A method according to claim 2 wherein the larvae are rootworms.

4. A method according to claim 3 wherein the rootworms are the Diabrotica species.

5. A method according to claim 2 wherein the larvae are cutworms.

6. A method according to claim 5 wherein the cutworms are the Agrotis species.

7. A method according to claim 1 wherein the larvae are wireworms.

8. A method according to claim 7 wherein the wireworms are the Agriotes species.

9. A method according to claim 1 wherein the phosphorothioate is applied by physically mixing with the topsoil.

10. A method according to claim 9 wherein the mixing is done concurrently with, preceded or followed by planting seeds which germinate into plants.

11. A method according to claim 1 wherein the phosphorothioate is applied to the soil habitat in the amount of about 0.01 kg/ha to about 11 kg/ha.

12. A method according to claim 11 wherein the phosphorothioate is applied to the soil habitat in the amount of about 0.1 to about 5 kg/ha.

13. A method according to claim 1 wherein the applying is done concurrently with planting of seeds which germinate into plants.

14. A method according to claim 1 wherein the applying is followed by planting of seeds which germinate into plants.

15. A method according to claim 1 wherein said soil habitat contains at least one of said insect larvae.

16. A method according to claim 1 wherein said growing plants are corn.

17. The method according to claim 16 wherein said insect larvae are selected from rootworms or cutworms.

18. The method according to claim 17 wherein said insect larvae are rootworms.

19. A method for controlling insect larvae selected from the group consisting of rootworms, cutworms, or wireworms, which inhabit soil and feed on growing plants, which comprises applying to the soil habitat of the larvae with or prior to the planting of seeds which germinate into said growing plants an insecticidally effective amount of the soil insecticide, O,O-diethyl-O-(1,2,2,2-tetrachloroethyl)phosphorothioate having persistence in the soil to effect said control of said insect larvae during the growing of said plants for at least 28 days.

20. A method for controlling insect larvae which inhabit soil and feed on growing corn plants selected from rootworms, cutworms, or wireworms which comprises applying to the soil habitat of the larvae with or prior to the planting of seeds which germinate into said growing corn plants an insecticidally effective amount of the soil insecticide, O,O-diethyl-O-(1,2,2,2-tetrachloroethyl)phosphorothioate having persistence in the soil to effect said control of said insect larvae during the growing of said corn plants for at least 28 days.

21. A method according to claim 21 wherein said phosphorothioate is applied by physically mixing with the topsoil.

22. A method for controlling insect larvae which inhabit the soil, selected from rootworms, cutworms or wireworms, which comprises applying to said larvae an insecticidally effective amount of O,O-diethyl O-(1,2,2-tetrachloroethyl)phosphorothioate.

23. A method according to claim 22 wherein the phosphorothioate is applied to the soil habitat of said rootworms, cutworms, or wireworms.

* * * * *